(12) United States Patent
Murai (10) Patent No.: US 10,112,037 B2
(45) Date of Patent: Oct. 30, 2018

(54) BLOOD CIRCUIT CONNECTOR

(71) Applicant: NIPRO CORPORATION, Osaka-shi, Osaka (JP)

(72) Inventor: Koichi Murai, Osaka (JP)

(73) Assignee: NIPRO CORPORATION, Osaka-shi, Osaka (JP)

( * ) Notice: Subject to any disclaimer, the term of this patent is extended or adjusted under 35 U.S.C. 154(b) by 0 days.

(21) Appl. No.: 15/320,017

(22) PCT Filed: Jun. 20, 2014

(86) PCT No.: PCT/JP2014/066417
§ 371 (c)(1),
(2) Date: Dec. 19, 2016

(87) PCT Pub. No.: WO2015/194032
PCT Pub. Date: Dec. 23, 2015

(65) Prior Publication Data
US 2017/0128711 A1     May 11, 2017

(51) Int. Cl.
*F16L 55/10*      (2006.01)
*A61M 39/12*      (2006.01)
(Continued)

(52) U.S. Cl.
CPC .......... *A61M 39/12* (2013.01); *A61M 1/3624* (2013.01); *A61M 39/28* (2013.01)

(58) Field of Classification Search
CPC ................................................... A61M 39/12
(Continued)

(56) References Cited

U.S. PATENT DOCUMENTS 3,120,879 A * 2/1964 Warner ................ F16N 21/02
                                                    184/91
3,199,748 A * 8/1965 Bross ................... B65D 47/10
                                                    215/307
(Continued)

FOREIGN PATENT DOCUMENTS

CN        202446549 U      9/2012
JP         61-37168 A      2/1986
(Continued)

OTHER PUBLICATIONS

Extended European Search Report, dated Jan. 26, 2018, for European Application No. 14895308.6.
(Continued)

*Primary Examiner* — James Hook
(74) *Attorney, Agent, or Firm* — Birch, Stewart, Kolasch & Birch, LLP (57) ABSTRACT

A blood circuit connector includes: a main body having a cylindrical shape and provided with a first opening end and a second opening end; a plug having a bottomed cylindrical shape and detachably attached to the first opening end; and a connection part configured to connect the main body and the plug. The plug includes a side wall loosely fitted to an outer circumferential surface of the first opening end. The connection part includes a curved part expanding in a direction away from the main body. In a state where the plug is attached to the first opening, the curved part is pushed in a direction approaching the outer circumferential surface of the main body such that the curved part extends, thereby cancelling a loosely fitted state between the side wall and the outer circumferential surface, so as to remove the plug from the first opening end.

4 Claims, 5 Drawing Sheets

(51) Int. Cl.
*A61M 1/36* (2006.01)
*A61M 39/28* (2006.01)

(58) Field of Classification Search
USPC ..... 138/89, 96 R; 604/263, 164.04, 192, 905
See application file for complete search history.

(56) References Cited

U.S. PATENT DOCUMENTS

| | | | |
|---|---|---|---|
| 5,385,372 A | | 1/1995 | Utterberg |
| 5,398,837 A | * | 3/1995 | Degrassi ................ B65D 51/04 215/306 |
| 5,951,519 A | * | 9/1999 | Utterberg .............. A61M 39/20 604/167.01 |
| 6,003,556 A | * | 12/1999 | Brugger ................ F16L 55/115 138/89 |
| 2007/0106229 A1 | * | 5/2007 | Wong .................. A61M 39/045 604/249 |
| 2010/0292673 A1 | | 11/2010 | Korogi et al. |
| 2012/0016318 A1 | | 1/2012 | Hoang et al. |

FOREIGN PATENT DOCUMENTS

| | | |
|---|---|---|
| JP | 7-47137 A | 2/1995 |
| JP | 10-328298 A | 12/1998 |
| JP | 2009-529629 A | 8/2009 |
| JP | 2010-279494 A | 12/2010 |
| JP | 2011-55911 A | 3/2011 |
| JP | 2013/530794 A | 8/2013 |
| WO | WO 03/011206 A1 | 2/2003 |
| WO | WO 2007/103998 A2 | 9/2007 |

OTHER PUBLICATIONS

Decision to Grant Patent for Japanese Application No. 2016-528750 dated Jul. 24, 2018 with English translation.
Chinese Office Action dated Aug. 31, 2018 for China Application No. 201480079986.4.

\* cited by examiner

BLOOD CIRCUIT CONNECTOR

TECHNICAL FIELD

The present invention relates to a blood circuit connector, and particularly to a blood circuit connector including: a main body provided with a through hole through which a tube can be inserted from both ends; and a plug connected to an outer circumferential surface of the main body, and allowing the plug to be detachably attached to one end of the main body.

BACKGROUND ART

An extracorporeal circulation circuit used for hemodialysis and the like is formed of an artery-side blood circuit and a vein-side blood circuit. The artery-side blood circuit includes a tube connected to one end of the hemodialyzer and used for connecting various kinds of devices. The tube has a tip end to which a blood circuit connector is attached, which is used for introducing another connector connected to an artery-side puncture needle. Also, the vein-side blood circuit includes a tube connected to the other end of the hemodialyzer and used for connecting various kinds of devices. The tube has a tip end to which a blood circuit connector is attached, which is used for introducing another connector connected to a vein-side puncture needle.

The blood circuit connector has a cylindrical shape provided with a through hole such that the above-described connector can be introduced into both ends thereof. Furthermore, it is preferable that the blood circuit connector is kept clean from the hygiene point of view. In particular, at one end of the blood circuit connector into which a connector connected to the artery-side puncture needle or the vein-side puncture needle is introduced, a plug for closing an opening at one end until use is provided in order to prevent contamination by various bacteria.

For example, Japanese Patent Laying-Open No. 2011-55911 (PTD 1) is cited as a document disclosing a blood circuit connector provided with a plug for closing an opening at one end.

The blood circuit connector disclosed in PTD 1 includes: a main body provided therein with a through hole and separable between one end and the other end; and a plug connected to the main body. The main body is provided at its one end with a first opening that communicates with the through hole. The plug is configured to close the first opening in the attached state where this plug is attached to the main body.

By the configuration as described above, the first opening can be closed by the plug until it becomes necessary to be used during the priming process or the like, so that the opening end of the main body located on the first opening side can be prevented from being contaminated by various bacteria.

CITATION LIST

Patent Document

PTD 1: Japanese Patent Laying-Open No. 2011-55911

SUMMARY OF INVENTION

Technical Problem

When the extracorporeal circulation circuit is used, a connector of the other blood circuit (including an adapter for connecting the connector) or a connector for a puncture needle is connected to one end of the main body of the blood circuit connector. In this case, it is necessary to remove the plug closing the opening at one end of the main body.

In the configuration disclosed in PTD 1, the blood circuit connector itself is not fixed. Accordingly, in order to allow disengagement between the main body and the plug, it becomes necessary to perform an operation of gripping the plug with one hand to pull out the plug while fixing the blood circuit connector with the other hand holding the main body, which requires exertion of considerable force with both hands. This operation also requires time and effort, which may lead to a significant overload.

The present invention has been made in light of the above-described problems. An object of the present invention is to provide a blood circuit connector that allows easy removal of a plug and also allows easy formation of an extracorporeal circulation circuit.

Solution to Problem

A blood circuit connector according to the present invention includes: a main body having a cylindrical shape and having a through hole provided therein to have one end provided with a first opening end and the other end provided with a second opening end; a plug having a bottomed cylindrical shape and detachably attached to the first opening end; and a connection part having flexibility and configured to connect the main body and the plug. The plug includes a side wall loosely fitted to an outer circumferential surface of the first opening end and a bottom facing the first opening end in an extending direction of an axis line of the main body in an attached state where the plug is attached to the first opening end. The connection part includes a first fixed end connected to the side wall of the plug, a second fixed end connected to an outer circumferential surface of the main body, and a curved part located between the first fixed end and the second fixed end and expanding in a direction away from the main body. In the attached state, the curved part is pushed in a direction approaching the outer circumferential surface of the main body such that the curved part extends, to cancel a loosely fitted state between the side wall of the plug and the outer circumferential surface of the first opening end, so as to remove the plug from the first opening end.

In the blood circuit connector according to the present invention, it is preferable that the connection part further includes an elastic force generating part located between the first fixed end and the curved part, and flexibly deformed in the attached state so as to generate elastic force. In this case, it is preferable that the plug is attached to the first opening end as the plug swings against the elastic force generated by the elastic force generating part such that an axis line of the plug extends in line with the axis line of the main body. It is preferable that, when the plug is removed, the loosely fitted state between the side wall of the plug and the outer circumferential surface of the first opening end is cancelled, to cause the plug to swing with restoring force produced based on the elastic force generated by the elastic force generating part, so as to move the plug away from above the axis line of the main body.

In the blood circuit connector according to the present invention, it is preferable that the elastic force generating part has an approximately S-shape.

In the blood circuit connector according to the present invention, it is preferable that the main body, the plug and the connection part are integrally molded by injection molding.

Advantageous Effects of Invention

According to the present invention, it becomes possible to provide a blood circuit connector that allows easy removal of a plug and also allows easy formation of an extracorporeal circulation circuit.

DESCRIPTION OF EMBODIMENTS

Embodiments of the present invention will be hereinafter described in detail with reference to the accompanying drawings. In the following embodiments, the same or corresponding components are designated by the same reference characters in the accompanying drawings, and description thereof will not be repeated.

Embodiments

Figure 1:
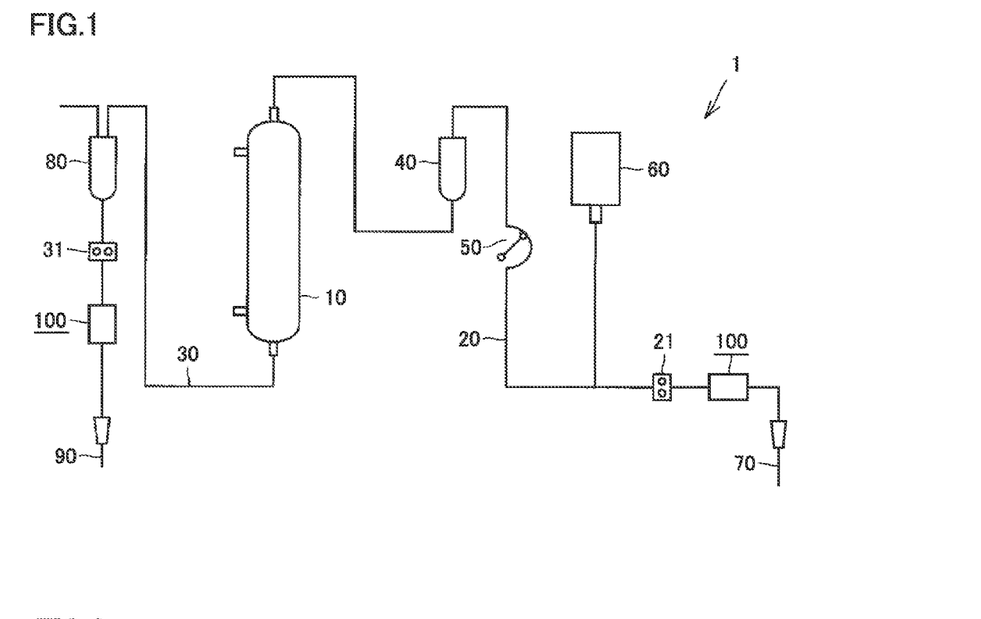
FIG. 1 is a schematic diagram of an extracorporeal circulation circuit in which a blood circuit connector is used, according to an embodiment of the present invention.

FIG. 1 is a schematic diagram of an extracorporeal circulation circuit in which a blood circuit connector is used, according to an embodiment of the present invention. Referring to FIG. 1, an extracorporeal circulation circuit 1 in which a blood circuit connector 100 according to the present embodiment is used will be hereinafter described.

As shown in FIG. 1, extracorporeal circulation circuit 1 in which blood circuit connector 100 according to the present embodiment is used is configured by connecting an artery-side blood circuit 20 to one end of a dialyzer 10, and connecting a vein-side blood circuit 30 to the other end of dialyzer 10.

Dialyzer 10 serves as a device for purifying blood by bringing blood and a dialysis fluid into contact with each other through a dialysis membrane, to cause diffusion by the concentration difference of solutes and ultrafiltration by the static pressure difference, thereby removing and supplying the solutes, and also removing moisture.

To artery-side blood circuit 20, an artery-side drip chamber 40, a physiological-saline supply part 60 for example filled with physiological saline and a blood circuit connector 100 are connected via a tube. Artery-side blood circuit 20 is set in a blood pump 50. To vein-side blood circuit 30, on the other hand, a vein-side drip chamber 80 and blood circuit connector 100 are connected via a tube.

Artery-side drip chamber 40 prevents air bubbles flowing through artery-side blood circuit 20 from flowing into dialyzer 10. Blood pump 50 delivers a circulation liquid within artery-side blood circuit 20 to dialyzer 10. Vein-side drip chamber 80 prevents air bubbles flowing through vein-side blood circuit 30 from flowing into a human body.

Before hemodialysis is carried out, a priming process is performed for washing the internal area of extracorporeal circulation circuit 1 to be used and the internal areas of various devices and processors incorporated therein with physiological saline or the like.

In the priming process, the passage from physiological-saline supply part 60 to the inside of blood circuit connector 100 located at the end of artery-side blood circuit 20 is first filled with physiological saline. Then, a clamp 21 is used to clamp a part of the tube that is located close to blood circuit connector 100, the tube serving to connect artery-side drip chamber 40 and the other end of blood circuit connector 100.

Then, blood pump 50 is operated to introduce physiological saline such that the physiological saline fills the passage through artery-side drip chamber 40, dialyzer 10 and vein-side drip chamber 80 to the inside of blood circuit connector 100 located at the end of vein-side blood circuit 30. Then, a clamp 31 is used to clamp a part of the tube that is located close to blood circuit connector 100, the tube serving to connect vein-side drip chamber 80 and the other end of blood circuit connector 100.

After the priming process is ended, in artery-side blood circuit 20, a connector of an artery-side puncture needle 70 is connected to one end of blood circuit connector 100. Also, in vein-side blood circuit 30, a connector of a vein-side puncture needle 90 is connected. Artery-side puncture needle 70 and vein-side puncture needle 90 are punctured in advance into a shunt blood vessel of a dialysis patient.

Figure 2:
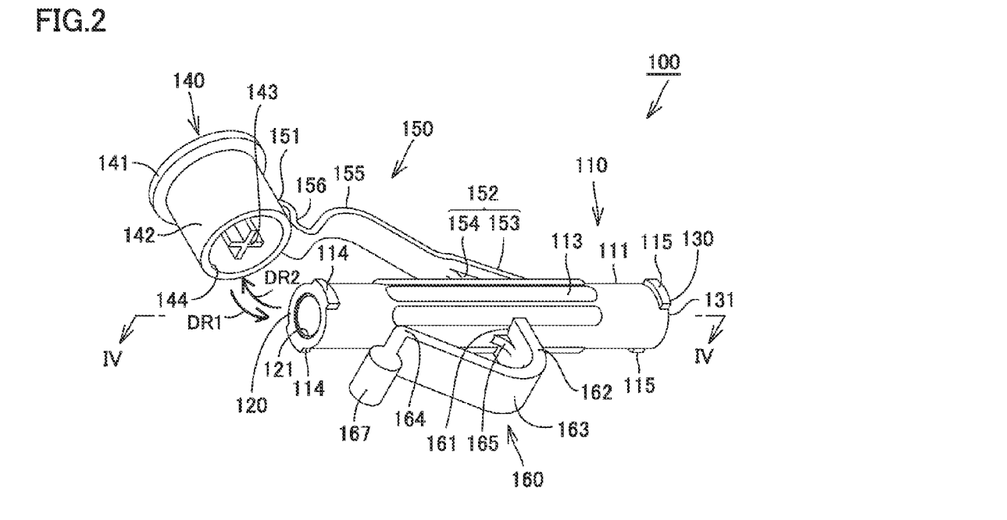
FIG. 2 is a perspective view of the blood circuit connector shown in FIG. 1.
Figure 3:
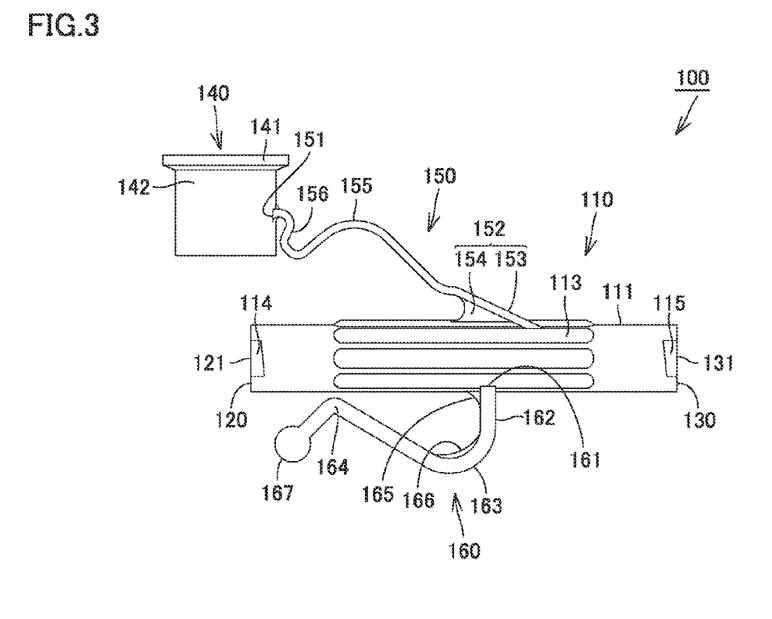
FIG. 3 is a front view of the blood circuit connector shown in FIG. 1.
Figure 4:
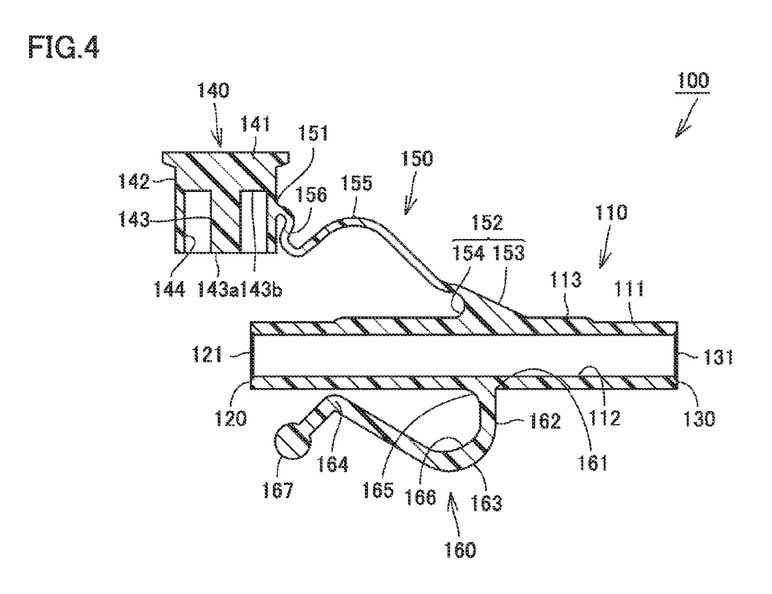
FIG. 4 is a cross-sectional view taken along a line IV-IV shown in FIG. 2.

FIG. 2 is a perspective view of the blood circuit connector shown in FIG. 1. FIG. 3 is a front view of the blood circuit connector shown in FIG. 1. FIG. 4 is a cross-sectional view taken along a line IV-IV shown in FIG. 2. Referring to FIGS. 2 to 4, blood circuit connector 100 according to the present embodiment will be hereinafter described.

As shown in FIGS. 2 to 4, blood circuit connector 100 according to the present embodiment includes a main body 110, a plug 140, a connection part 150, and a hook 160. Blood circuit connector 100 is for example formed of an injection-molded product that is obtained by integrally molding main body 110, plug 140, connection part 150, and hook 160. Furthermore, the material of blood circuit connector 100 may be synthetic resins such as plastic, for example.

Main body 110 is formed in a cylindrical shape and provided with a through hole 112 (see FIG. 4) so as to have one end provided with a first opening end 120 and the other end provided with a second opening end 130. Main body 110 has an outer circumferential surface 111 provided with a plurality of bar-shaped protrusions 113. The plurality of bar-shaped protrusions 113 are spaced apart from each other in the circumferential direction of the main body and extend in the extending direction of the axis line of main body 110.

First opening end 120 of main body 110 is provided with a first opening 121 located as one end of through hole 112. Second opening end 130 of main body 110 is provided with a second opening 131 located as the other end of the through hole.

Outer circumferential surface 111 of main body 110 on the first opening end 120 side and outer circumferential surface 111 of main body 110 on the second opening end 130 side are provided with a pair of engagement parts 114 and a pair of engagement parts 115, respectively, that extend in the circumferential direction of main body 110 and that protrude in the direction vertical to the extending direction of the axis line of main body 110.

Engagement parts 114 as one pair are provided so as to face each other in the direction vertical to the extending direction of the axis line of main body 110. Similarly, engagement parts 115 as one pair are also provided so as to face each other in the direction vertical to the extending direction of the axis line of main body 110. In addition, the pair of engagement parts 114 may be used as a thread part for connecting the connector of a puncture needle, for example.

Plug 140 has a bottomed cylindrical shape that is detachably attached to first opening end 120. Plug 140 includes: a bottom 141 formed in a circular shape and a positioning part 143 formed in a cross shape, both of which are seen in the axial direction of plug 140; and a side wall 142 formed in a cylindrical shape and extending from the main surface of bottom 141 in the direction vertical to the main surface. Bottom 141, side wall 142 and positioning part 143 are disposed such that their central axes extend coaxially with each other.

The outer diameter of side wall 142 is smaller than the outer diameter of bottom 141, so that the circumferential edge of bottom 141 protrudes from side wall 142 in the circumferential direction. Furthermore, positioning part 143 is disposed on the inside of side wall 142. The outside dimension of positioning part 143 on the side of an end 143*a* (see FIG. 4) is smaller than the inner diameter of side wall 142. The outside dimension of positioning part 143 on the side of a base part 143*b* (see FIG. 4) is approximately the same as the inner diameter of side wall 142.

Thereby, in the attached state where plug 140 is attached to first opening end 120 of main body 110 (see FIGS. 5 and 6), a housing space 144 is to be formed on the end 143*a* side of positioning part 143. Housing space 144 serves to house first opening end 120 between positioning part 143 and side wall 142. Furthermore, in the attached state (see FIGS. 5 and 6), a portion of positioning part 143 on the base part 143*b* side is almost in contact with first opening end 120. Thereby, the position of plug 140 to be attached is determined.

Connection part 150 serves as a part for connecting main body 110 and plug 140. Furthermore, connection part 150 has flexibility and has a plate-like shape that is partially curved. Connection part 150 is extended and contracted, so that plug 140 can be moved in a DR1 direction (see FIG. 2) so as to be attachable to first opening end 120 of main body 110, and so that attached plug 140 can be moved in a DR2 direction (see FIG. 2) so as to be removable from first opening end 120. In this way, plug 140 is configured so as to be swingable.

Connection part 150 includes: a first fixed end 151 coupled to side wall 142 of plug 140; a second fixed end 152 coupled to outer circumferential surface 111 of main body 110; and a curved part 155 and an elastic force generating part 156 that are located between first fixed end 151 and second fixed end 152 and arranged sequentially from second fixed end 152.

In a front view of blood circuit connector 100 from which plug 140 has been removed (see FIG. 3), first fixed end 151 is located approximately in the center of the outer side surface of side wall 142 that is located close to main body 110. In the attached state where plug 140 is attached, first fixed end 151 and second fixed end 152 are arranged so as to align in the extending direction of the axis line of main body 110.

Second fixed end 152 includes: a linear-shaped inclined part 153 that is inclined in the direction away from main body 110; and a reinforcement part 154 that connects the approximately center portion of inclined part 153 and outer circumferential surface 111 of main body 110 along the extending direction of the axis line of main body 110. Thereby, second fixed end 152 is firmly fixed to outer circumferential surface 111 of main body 110.

Curved part 155 is provided so as to expand in the direction away from main body 110. Curved part 155 is extendable and contractable, and formed such that the curvature of curved part 155 in the attached state is greater than the curvature of curved part 155 in the removed state.

Elastic force generating part 156 has an approximately S shape including a curved part expanding toward first fixed end 151. Elastic force generating part 156 is located between first fixed end 151 and curved part 155, and flexibly deformed in the attached state so as to generate elastic force.

Hook 160 serves as a part to be inserted into an orifice of a container for fixation (see FIG. 12) when the physiological saline or the circulation liquid is discharged through first opening end 120 during the priming process or after completion of hemodialysis.

Hook 160 is arranged so as to face connection part 150 with main body 110 interposed therebetween. Hook 160 includes a fixed end 161 and a free end 167. Furthermore, hook 160 has flexibility and includes: a plate-shaped part that is partially curved and bent; and a sphere-shaped part that is located at free end 167 (the tip end).

The above-described plate-shaped part of hook 160 includes: a linear part 162 extending from outer circumferential surface 111 of main body 110 in the direction vertical to the extending direction of the axis line of main body 110; a curved part 163 expanding in the direction away from main body 110; and a bent part 164 bent in the direction away from main body 110.

In order to ensure the strength, linear part 162 and curved part 163 are provided with reinforcement parts 165 and 166, respectively, so as to be approximately centered on their respective surfaces extending toward main body 110. Furthermore, a gap is provided between bent part 164 and main body 110, and the orifice of the container can be inserted into this gap.

In the state where the orifice of the container is inserted into the gap, hook 160 is flexibly deformed such that bent part 164 is moved away from main body 110.

Figure 5:
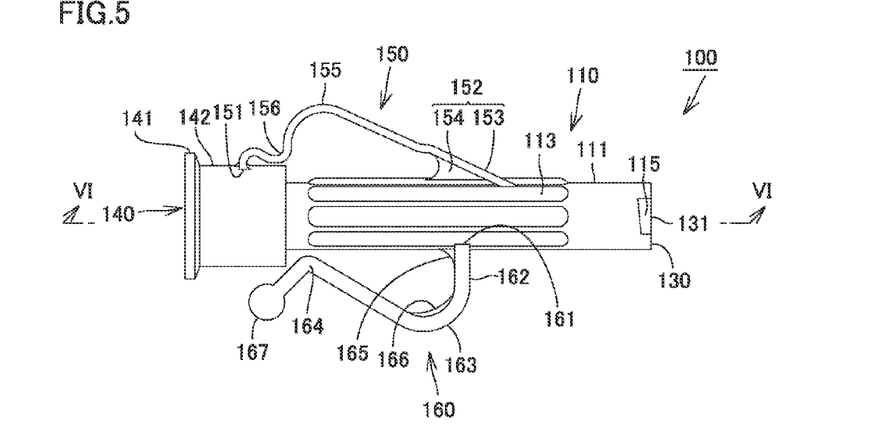
FIG. 5 is a schematic diagram showing the attached state where a plug is attached to a first opening end of a main body in the blood circuit connector shown in FIG. 1.

FIG. 5 is a schematic diagram showing the attached state where the plug is attached to the first opening end of the main body in the blood circuit connector shown in FIG. 1.

Figure 6:
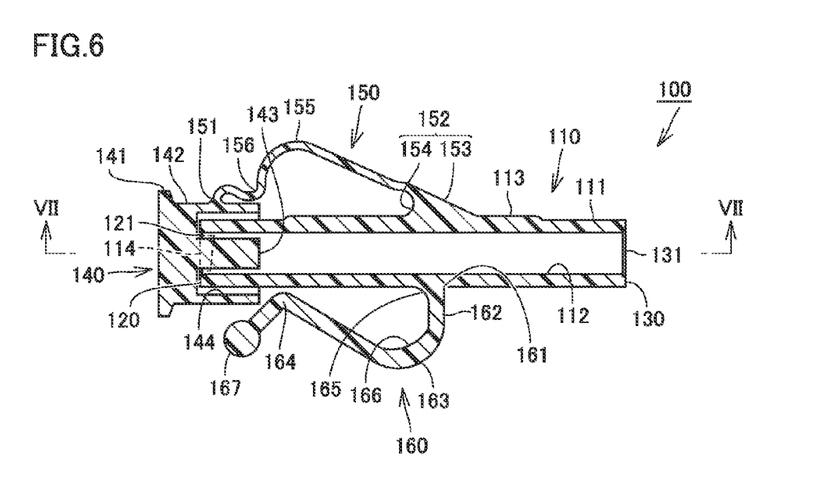
FIG. 6 is a cross-sectional view taken along a line VI-VI shown in FIG. 5.
Figure 7:
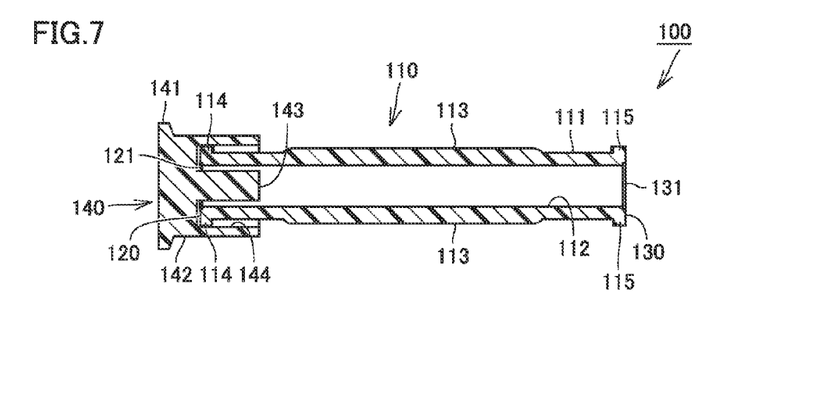
FIG. 7 is a cross-sectional view taken along a line VII-VII shown in FIG. 6.

FIG. 6 is a cross-sectional view taken along a line VI-VI shown in FIG. 5. FIG. 7 is a cross-sectional view taken along a line VII-VII shown in FIG. 6. Referring to FIGS. 5 to 7, an explanation will be hereinafter given with regard to the attached state where plug 140 is attached to first opening end 120 in blood circuit connector 100.

As shown in FIGS. 5 to 7, in the attached state where plug 140 is attached so as to close first opening end 120, bottom 141 of plug 140 is disposed so as to face first opening end 120 in the extending direction of the axis line of main body 110, and first opening end 120 is housed in housing space 144.

As shown in FIG. 7, in the state where first opening end 120 is housed in housing space 144, a pair of engagement parts 114 comes in contact with the inner side surface of side wall 142, so that plug 140 engages with first opening end 120. In this case, as shown in FIG. 6, a gap is provided between the inner circumferential surface of first opening end 120 and each of end 143a of positioning part 143 and the inner side surface of side wall 142, so that side wall 142 of plug 140 is loosely fitted to outer circumferential surface 111 of first opening end 120.

Furthermore, when plug 140 is attached to first opening end 120, connection part 150 is flexibly deformed, and thus, plug 140 is attached to first opening end 120 while swinging against the elastic force generated by elastic force generating part 156 such that the axis line of plug 140 extends in line with the axis line of main body 110. Thereby, elastic force generating part 156 maintains the state where plug 140 is biased in the DR2 direction (see FIG. 2).

Figure 8:
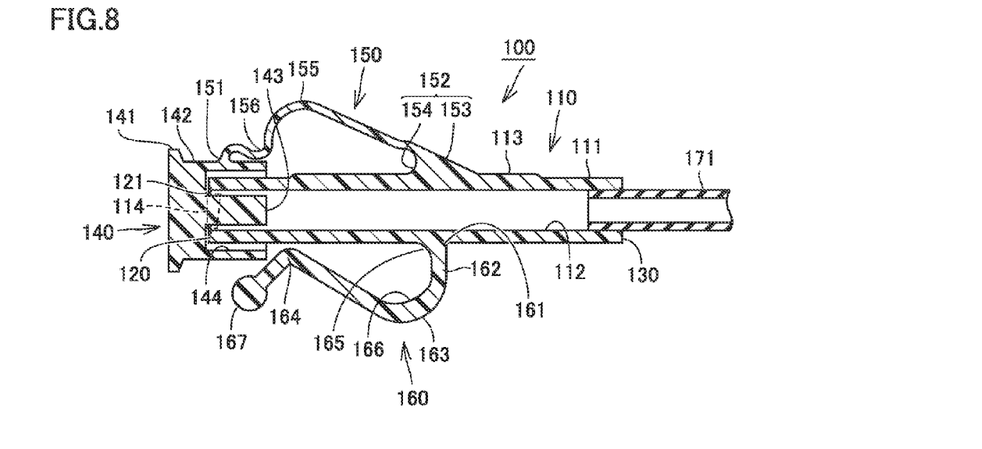
FIG. 8 is a cross-sectional view showing the state where a tube is introduced into the other end of the blood circuit connector from the state shown in FIG. 5.

FIG. 8 is a cross-sectional view showing the state where a tube is introduced into the other end of the blood circuit connector from the state shown in FIG. 5. Referring to FIG. 8, an explanation will be hereinafter given with regard to the state where a tube 171 is introduced into the other end of the blood circuit connector.

As shown in FIG. 8, when extracorporeal circulation circuit 1 is formed, blood circuit connector 100 is prepared, into which tube 171 forming a part of artery-side blood circuit 20 (see FIG. 1) or vein-side blood circuit 30 (see FIG. 1) is inserted in advance through second opening end 130. In this state, plug 140 is attached to first opening end 120. It is to be noted that tube 171 is liquid-tightly inserted into through hole 112.

Figure 9:
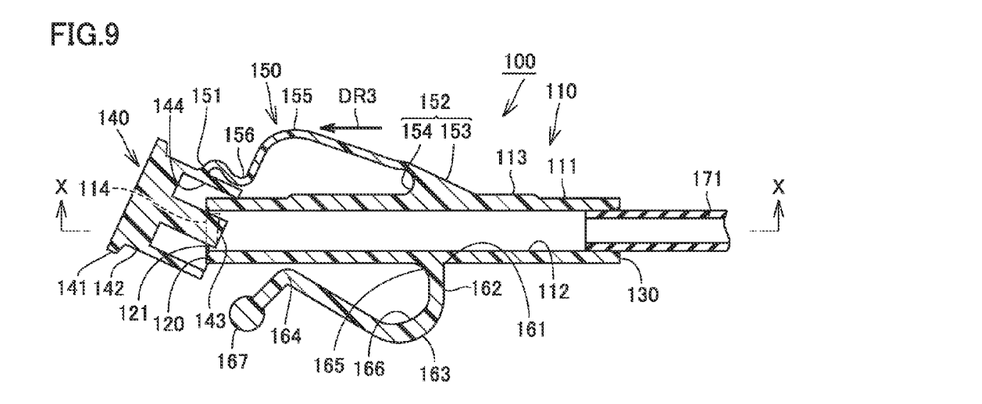
FIG. 9 is a cross-sectional view showing the manner in which a curved part of a connection part in the blood circuit connector is pushed so as to be moved from the state shown in FIG. 8.
Figure 10:
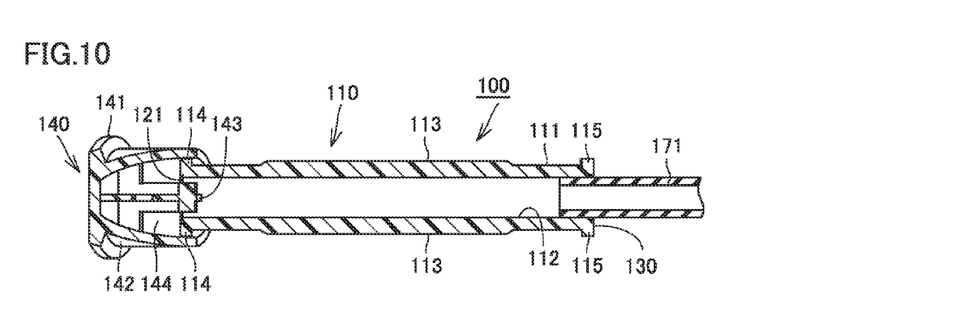
FIG. 10 is a cross-sectional view taken along a line X-X shown in FIG. 9.
Figure 11:
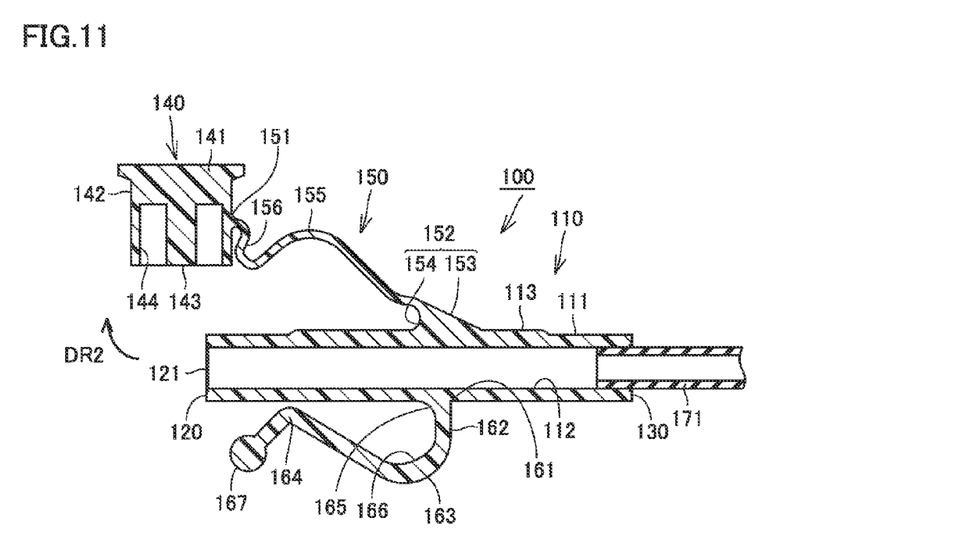
FIG. 11 is a cross-sectional view showing the state where the plug is removed from the first opening end of the main body in the blood circuit connector.

FIG. 9 is a cross-sectional view showing the manner in which the curved part of the connection part in the blood circuit connector is pushed to be moved from the state shown in FIG. 8. FIG. 10 is a cross-sectional view taken along a line X-X shown in FIG. 9. FIG. 11 is a cross-sectional view showing the state where the plug is removed from the first opening end of the main body in the blood circuit connector. Referring to FIGS. 9 to 11, the operation for removing plug 140 from first opening end 120 will be hereinafter described.

As shown in FIG. 9, when plug 140 is removed from first opening end 120, curved part 155 of connection part 150 is pushed in the direction approaching outer circumferential surface 111 of main body 110. In this case, the user uses his/her index finger or middle finger of one hand to grip hook 160 so as to be covered, and then, uses his/her thumb to push curved part 155 to be moved, for example, in a DR3 direction shown in the figure. Thereby, curved part 155 is extended, so that plug 140 moves away from hook 160 and swings in the direction back to the removed state (the DR2 direction: see FIG. 2).

While plug 140 is swinging, plug 140 is inclined such that the end of side wall 142 of plug 140 is positioned in the manner in which its tip end on the connection part 150 side is located closer to second opening end 130 than its tip end on the hook 160 side is. Between the inner side surface of side wall 142 and outer circumferential surface 111 of main body 110, and between positioning part 143 and the inner circumferential surface of main body 110, a gap is provided such that plug 140 is swingable relative to first opening end 120.

In this state, as shown in FIG. 10, since a pair of engagement parts 114 comes in contact with the inner side surface of side wall 142 of plug 140, the loosely fitted state between side wall 142 and first opening end 120 is not canceled.

When curved part 155 of connection part 150 is further pushed with a thumb in the direction approaching outer circumferential surface 111 of main body 110 as described above, curved part 155 is further extended, so that plug 140 swings to a position at which the pair of engagement parts 114 does not come in contact with the inner side surface of side wall 142 of plug 140. Thereby, the loosely fitted state between side wall 142 of plug 140 and first opening end 120 is cancelled.

As shown in FIG. 11, when the loosely fitted state between side wall 142 of plug 140 and first opening end 120 is canceled, the restoring force obtained based on the elastic force generated by elastic force generating part 156 causes plug 140 to further swing in the DR2 direction such that plug 140 is moved away from above the axis line of main body 110. Thereby, plug 140 moves in the extending direction of the axis line of the main body to a position at which this plug 140 does not overlap with main body 110.

In this way, plug 140 can be readily removed from main body 110 in a single-touch operation of pushing connection part 150 in the direction approaching main body 110. Since such a single-touch operation can be performed only with one hand, plug 140 can be removed more smoothly. Thus, it becomes possible to eliminate the time and effort caused when one hand is used to grip and remove plug 140 while using the other hand to fix main body 110 as in the conventional case.

Figure 12:
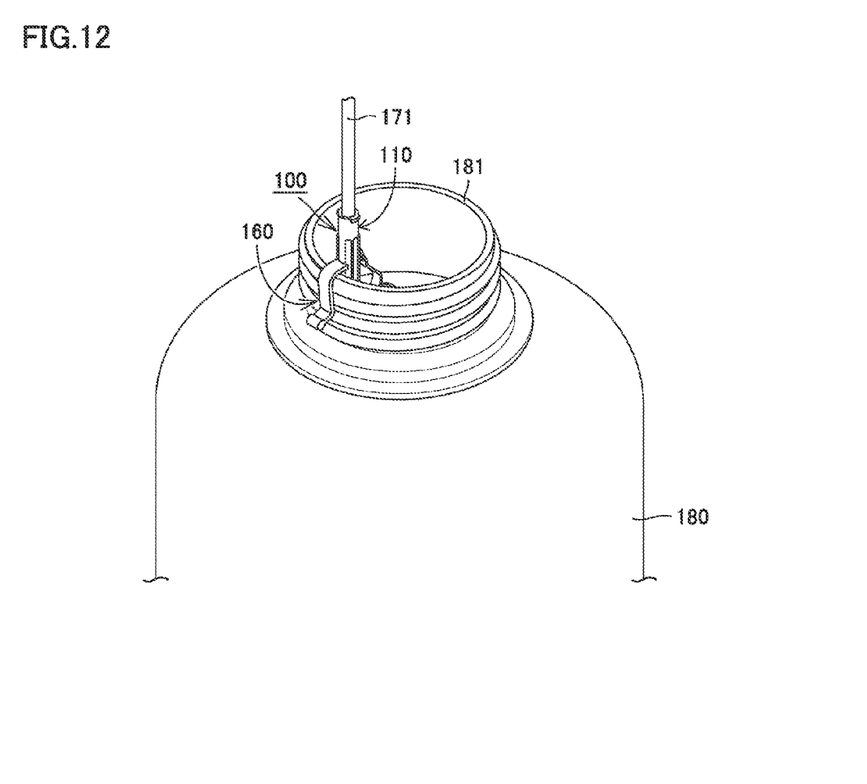
FIG. 12 is a schematic diagram showing an example of the state where the blood circuit connector is used during a priming process.

FIG. 12 is a schematic diagram showing an example of the state where the blood circuit connector is used during a priming process. Referring to FIG. 12, an explanation will be hereinafter given with regard to an example of the state where the blood circuit connector is used during the priming process.

As shown in FIG. 12, in the state where tube 171 is inserted through second opening end 130, and in the state where plug 140 is removed from first opening end 120 of main body 110, hook 160 is hooked on an orifice 181 of a container 180 such that first opening end 120 faces the inside of container 180.

By hooking blood circuit connector 100 on container 180 so as to be attached thereto, the physiological saline and the like having circulated through extracorporeal circulation circuit 1 can be discharged into container 180. In addition, also when hemodialysis is completed, blood circuit connector 100 is attached to orifice 181 of container 180 as described above, so that the circulation liquid can be discharged.

In this way, when the physiological saline and the circulation liquid are discharged, plug 140 does not overlap with main body 110 in the extending direction of the axis line of the main body, with the result that the physiological saline and the circulation liquid can be readily discharged through first opening end 120.

By the configuration as described above, in blood circuit connector 100 according to the present embodiment, connection part 150 is pushed to be moved closer to main body 110, so that plug 140 can be readily removed from first opening end 120. Furthermore, an extracorporeal circulation circuit can be readily formed by using blood circuit connector 100 according to the present embodiment.

As described above, blood circuit connector 100 according to the present embodiment has been described while illustrating the configuration including elastic force generating part 156, but the configuration not including elastic force generating part 156 may be applied. Also in such a configuration, curved part 155 is coupled to the end on the outer side surface of side wall 142 of plug 140 that is located on the opposite side to bottom 141, so that plug 140 can be readily removed from first opening end 120 while utilizing the elastic force caused by flexible deformation of curved part 155.

Although the embodiments of the present invention have been described as above, the embodiments disclosed herein are illustrative and non-restrictive in every respect. The scope of the present invention is defined by the terms of the claims, and is intended to include any modifications within the meaning and scope equivalent to the terms of the claims.

REFERENCE SIGNS LIST

1 extracorporeal circulation circuit, 10 dialyzer, 20 artery-side blood circuit, 21, 31 clamp, 30 vein-side blood circuit, 40 artery-side drip chamber, 50 blood pump, 60 physiological-saline supply part, 70 artery-side puncture needle, 80 vein-side drip chamber, 90 vein-side puncture needle, 100 blood circuit connector, 110 main body, 111 outer circumferential surface, 112 through hole, 113 protrusion, 114, 115 engagement part, 120 first opening end, 121 first opening, 130 second opening end, 131 second opening, 140 plug, 141 bottom, 142 side wall, 143 positioning part, 143*a* end, 143*b* base part, 144 housing space, 150 connection part, 151 first fixed end, 152 second fixed end, 153 inclined part, 154 reinforcement part, 155 curved part, 156 elastic force generating part, 160 hook, 161 fixed end, 162 linear part, 163 curved part, 164 bent part, 165 reinforcement part, 167 free end, 171 tube.

The invention claimed is:

1. A blood circuit connector comprising;
   a main body having a cylindrical shape, the main body having a through hole provided therein to have one end provided with a first opening end and the other end provided with a second opening end;
   a plug having a bottomed cylindrical shape and detachably attached to the first opening end; and
   a connection part having flexibility and configured to connect the main body and the plug,
   the plug including a side wall loosely fitted to an outer circumferential surface of the first opening end and a bottom facing the first opening end in an extending direction of an axis line of the main body in an attached state where the plug is attached to the first opening end,
   the connection part including a first fixed end connected to the side wall of the plug, a second fixed end connected to an outer circumferential surface of the main body, and a curved part located between the first fixed end and the second fixed end and expanding in a direction away from the main body, and
   in the attached state, the curved part being pushed in a direction approaching the outer circumferential surface of the main body such that the curved part extends, to cancel a loosely fitted state between the side wall of the plug and the outer circumferential surface of the first opening end, so as to remove the plug from the first opening end.

2. The blood circuit connector according to claim 1, wherein
   the connection part further includes an elastic force generating part located between the first fixed end and the curved part, and flexibly deformed in the attached state so as to generate elastic force,
   the plug is attached to the first opening end such that an axis line of the plug extends in line with the axis line of the main body as the plug swings against the elastic force generated by the elastic force generating part, and
   when the plug is removed, the loosely fitted state between the side wall of the plug and the outer circumferential surface of the first opening end is cancelled, to cause the plug to swing with restoring force produced based on the elastic force generated by the elastic force generating part, so as to move the plug away from above the axis line of the main body.

3. The blood circuit connector according to claim 2, wherein the elastic force generating part has an approximately S-shape.

4. The blood circuit connector according to claim 1, wherein the main body, the plug and the connection part are integrally molded by injection molding.

* * * * *